United States Patent [19]
Faubl

[11] 3,950,390
[45] Apr. 13, 1976

[54] 1-HYDROXY-3-CYCLOPENTENE CARBOXYLIC ACID

[75] Inventor: Hermann Faubl, Mystic, Conn.

[73] Assignee: Pfizer Inc., New York, N.Y.

[22] Filed: Aug. 26, 1974

[21] Appl. No.: 500,804

Related U.S. Application Data

[62] Division of Ser. No. 370,337, June 15, 1973, Pat. No. 3,852,322.

[52] U.S. Cl.................. 260/468 K; 260/514 K
[51] Int. Cl.²............... C07C 61/32; C07C 67/74
[58] Field of Search.................. 260/468 K, 514 K

[56] References Cited
UNITED STATES PATENTS

3,714,248  1/1973  Alburn.............................. 260/557

Primary Examiner—Robert Gerstl
Attorney, Agent, or Firm—Francis X. Murphy; Charles J. Knuth; Albert E. Frost

[57] ABSTRACT

A new process for the production of citric acid, and intermediates therefor of the formula:

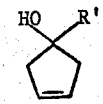

wherein R' is cyano or CO-R², wherein R² is lower alkoxy, amino or hydroxy.

4 Claims, No Drawings

1-HYDROXY-3-CYCLOPENTENE CARBOXYLIC ACID

CROSS-REFERENCE TO RELATED APPLICATIONS

This application is a division of my application Ser. No. 370,337, filed June 15, 1973, now U.S. Pat. No. 3,852,322.

BACKGROUND OF THE INVENTION

1. Field of the Invention

This invention relates to citric acid, and more specifically to a new chemical process for the production of citric acid which utilizes novel cyclopentene derivatives.

2. Description of the Prior Art

Citric acid, by virtue of its palatability, low toxicity and ease of assimilation, has become one of the most widely used acidulants in the food and pharmaceuticals industries. Both the acid and its salts find use in beverages, jams, jellies and gelatin preparations. Sodium citrate is particularly valuable as a sequestering agent in detergents.

Citric acid is usually produced by fermentation methods, using, for example *Aspergillus niger* or a yeast of the genus Candida. There are also several chemical methods known for the synthesis of citric acid. Haller and Held, Ann. Chim. Phys., 23 145 (1891), reported a method starting from β-ketoglutaric acid, and Dunschmann, Justus Liebigs Ann. Chem., 261, 162 (1891), described a similar method utilizing diethyl β-ketoglutarate. Fischer and Dangschat, Helv. Chim. Acta, 17, 1196 (1934), obtained citric acid from quinic acid, and Baer et al., J. Amer. Chem. Soc., 61, 2607 (1939), showed that the methyl ester of quinic acid can also be converted into citric acid. Belgian Pat. No. 784,238 discloses a process involving the oxidation of 3-methylene-1,5-pentanediol or several of its chemical equivalents.

Summary of the Invention

It has now been found that citric acid can be produced from the known ketone, 3-cyclopenten-1-one, by a new series of reactions comprising: (1) preparation of the novel compound of formula I; (2) conversion of the

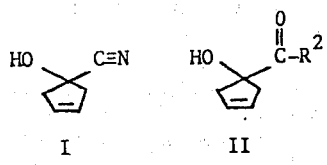

compound of formula I into a novel compound of the formula II, wherein $R_2$ is lower alkoxy, amino or hydroxy, amino or hydroxy; and (3) oxidative cleavage of the carbon-carbon double bond of the said compound of the formula II, with concomitant formation of two carboxylic acid groups, followed, if necessary, by hydrolysis. The said hydrolysis is necessary in the cases wherein $R^2$ is lower alkoxy, for example, methoxy or ethoxy, or amino, but not wherein $R^2$ is hydroxy.

By the term lower alkoxy is meant straight- and branched-chain alkoxy groups having from one to ten carbon atoms. However, because of the cheapness and ready availability of the starting materials, straight- and branched-chain alkoxy groups having from one to five carbon atoms are particularly preferred.

DETAILED DESCRIPTION OF THE INVENTION

The novel compound of formula I is prepared from 3-cyclopentenone by reaction with hydrogen cyanide. The hydrogen cyanide may be present in the form of a salt, for example an alkali metal salt, such as the sodium or the potassium salt; or a mixture of the free acid and a salt may be used. The reactants can be contracted in the absence of solvent, or, if desired, a solvent which does not adversely react with either the reactants or products may be used. Appropriate solvents are, for example, water, lower alkanoic acids (e.g. acetic acid), lower alkanols (e.g. ethanol) and N,N-dimethylformamide, or mixtures of these solvents. The reaction is normally carried out at a temperature in the range from about −20° C. to about 50° C., and preferably in the range of from −10° C. to 10° C. It is usually convenient to employ a several-molar excess of hydrogen cyanide, in order to ensure complete conversion of the ketone into its cyanohydrin. However, the use of an excess of hydrogen cyanide is not essential for the success of the reaction, and equimolar proportions of cyanide and ketone, or even an excess of ketone, can be employed. In the latter instance, some unreacted ketone will remain at the end of the reaction. When the ketone and hydrogen cyanide are contacted at around 0° C., the reaction usually complete within a few hours. Clearly, the reaction will proceed more quiclky at higher temperatures. In the cases where lower temperature are used, it may be necessary to allow the reaction to proceed for a longer period to ensure complete reaction. If the hydrogen cyanide is used largely in the form of a salt, and if an acidic solvent such as an alkanoic acid is not employed, it is necessary to acidify the reaction medium prior to work-up to ensure a good yield of cyanohydrin. Recovery of the product can normally be accomplished simply be removal of the solvents by evaporation. If desired, the crude product can then be purified by methods well-known in the art. However, in most instances extensive purification is not required and, indeed, it is possible to utilize the cyanohydrin in situ without isolation.

In the above-described method for cyanohydrin formation, the 3-cyclopentenone can successfully be replaced by its bisulfite addition product. The said bisulfite addition product is readily prepared from the ketone by methods well-known in the art. Thus, for example, the ketone is reacted with an excess of sodium meta-bisulfite in an inert solvent, such as a lower alkanol, at or around ambient temperature.

The starting ketone, namely 3-cyclopenten-1-one, can be obtained, for example, by the method of Hess and Brown, J. Org. Chem., 32, 4138 (1967), or of Hess and Pitts, J. Amer. Chem. Soc., 89, 1973 (1967).

The compound of formula I is converted into a compound of the formula II, wherein $R^2$ is lower alkoxy, via reaction with a lower alkanol in the presence of an acid catalyst, followed by treatment with an excess of water. Both branched- and straight-chain alkanols, having from one to ten carbon atoms, can be used in the first step of this sequence. However, the alkanols which are particularly suitable are both branched- and straight-chain alkanols having from one to five carbon atoms, for example, methanol and ethanol. The alkanol is often used as its own solvent, although it can be used in admixture with a co-solvent such as an ether, for example, diethyl ether or dioxane; a chlorinated hydrocarbon, for example, chloroform or methylene chloride; or an aromatic hydrocarbon, for example, benzene or toluene. Indeed, the use of a co-solvent becomes a preferred embodiment in those cases where it is desired to utilize an alkanol which exists in the solid state at or around ambient temperature. In most cases, the alkanol is present in large excess. However, smaller amounts, even as low as one molar equivalent, can be used successfully. The temperature at which the alkanolysis is conducted is not critical, and temperatures in the range from about 0° C. to 100° C. can be used. Temperatures at or around room temperature are particularly convenient. In the latter case, the reaction is normally complete after several hours, although if a small molar ratio of alkanol to nitrile is used reaction times as long as several days or weeks may be required. The addition of water after the alkanolysis step completes the conversion into ester. As will be appreciated by one skilled in the art, however, the ester product should not be exposed to an excess of aqueous acid for a prolonged period since there is a danger in this case of causing substantial hydrolysis to carboxylic acid. In any event, the crude ester product is sometimes contaminated with carboxylic acid. A wide variety of acid catalysts can be used in this process, such as, for example, a mineral acid, an anhydrous hydrohalic acid or a sulfonic acid. Representative examples of such acids are sulfuric acid, hydrogen chloride and p-toluenesulfonic acid. The amount of acid present is usually in the range 0.1 to 1.0 mole per mole of nitrile used, but larger amounts can be employed. Recovery of the ester product is usually achieved simply by partitioning the reaction product between an appropriate organic solvent and an aqueous alkaline phase. Separation and evaporation of the organic phase then affords the ester product, which can either be used directly for the next step or, if desired, purified further by methods well-known in the art.

The compound of formula I is converted into a compound of formula II, wherein $R^2$ is amino, by hydrolysis. The said hydrolysis is carried out by treating the nitrile with water in the presence of an acid catalyst. The proportion of water used must be at least one molar equivalent based on the nitrile used, and will not normally exceed about twenty molar equivalents. A solvent which dissolves both the nitrile and the water, but which does not react with the nitrile in the presence of an acid catalyst, is usually used. Representative examples of such solvents are a lower alkanoic acid, for example, acetic acid, or a water-miscible ether, for example, 1,2-dimethoxyethane. The reaction is normally conducted at or around room temperature, and it is normally complete within a few hours, for example, overnight. A wide variety of acid catalysts can be used, for example, those of the type used in the conversion of the compound of formula I to a compound of formula II, whherein $R^2$ is lower alkoxy, which are enumerated above. The product is normally recovered by methods similar to those used for compounds of the formula II, wherein $R^2$ is lower alkoxy.

Conversion of the compound of formula I into the compound of formula II, wherein $R^2$ is hydroxy, is also effected by contacting the compound of formula I with water in the presence of an acid catalyst. In this case, however, a large excess of water (greater than about twenty molar equivalents) is normally used, and in fact it is a convenient procedure to utilize sufficient water that a further co-solvent is not necessary. However, those co-solvents which are miscible with water, dissolve the nitrile and do not react with a nitrile in the presence of an acid can be used. Further, in the instant hydrolysis, somewhat higher temperatures are employed. The hydrolysis is usually conducted in the temperature range of from about 50° C. to about 150° C. and typically at about 100° C. At around 100° C., the hydrolysis commonly requires a reaction time of several hours for complete conversion into acid. For product recovery, the solvents are evaporated in vacuo leaving the product in a crude state. It can either be purified by methods well-known in the art or used directly in the next step. A particularly convenient method of product purification involves formation and decomposition of salts of the said acid.

An alternate route to the compound of the formula II, wherein $R^2$ is hydroxy, is by hydrolysis of a compound of formula II, wherein $R^2$ is lower alkoxy or amino. Although the methods described earlier for the production of the compound of formula II, wherein $R^2$ is hydroxy, from the compound of formula I can conveniently be used for this hydrolysis, hydrolysis under basic conditions can also be employed. In the latter instance the said compound of formula II, wherein $R^2$ is lower alkoxy or amino, is treated with water in the presence of a basic catalyst. At least one molar equivalent of water is required, but it is quite common to use a large excess of water. Although sufficient water is often present to obviate the need for a further diluent, co-solvents such as, for example, lower alkanols (e.g. methanol and ethanol) can be used. The basic catalyst, which can be a wide variety of agents such as, for example, alkali metal hydroxides or carbonates (e.g. potassium hydroxide or potassium carbonate) or alkaline earth metal hydroxides (e.g. barium hydroxide), will normally be present to the extent of about at least one molar equivalent. However, larger proportions, up to around ten molar equivalents, can be used. The reaction is usually conducted at a temperature in the range from about 50° C. to about 150° C., and preferably at around 100° C. It usually takes a reaction time of several hours to ensure complete hydrolysis.

The compound of formula II, wherein $R^2$ is hydroxy, is converted into citric acid by oxidative cleavage of the carbon-carbon double bond of the said compound of formula II, with concomitant formation of two carboxylic acid groups. Conversion of a compound of formula II, wherein $R^2$ is lower alkoxy or amino, into citric acid involves the same oxidative cleavage reaction, which is then followed by a hydrolysis step.

The oxidant to be used for the said oxidation step can be chosen from a wide variety of reagents well-known in the art. A particularly convenient oxidant which can be used, however, is potassium permanganate. In this case, the compound of formula II, wherein $R^2$ is lower alkoxy, amino or hydroxy, is usually treated with at least about three molar equivalents of potassium permanganate in an appropriate solvent, such as, for example, water. Larger quantities of oxident are sometimes used. The reaction is conducted in the temperature range from about 0° C. to about 80° C., and preferably at about 25° C. It commonly requires a few hours to reach completion at around ambient temperatures and, in order to hasten completion of reaction, further quantities of oxidant can be added during the course of the reaction. If desired, a cosolvent which is miscible with water but does not interact with potassium permanganate can be used. Representative of such co-solvents are acetone or a water-miscible ether such as 1,2-dimethoxyethane, tetrahydrofuran or dioxane. If it is desired to work under completely non-aqueous conditions, a particularly convenient method, as regards ease of operation, involves the use of a macrocyclic polyether of the so-called "crown-ether" type. Thus, for example, using dicyclohexyl-18-crown-6 (an item of commerce) it is possible to use benzene as solvent.

A further oxidant which is useful for the oxidative cleavage of the double bond of the said compound of formula II is nitric acid. In this instance, the said compound of formula II is treated with nitric acid of strength within the range from about 30% to about 90% by weight, and preferably from about 60% to 80% by weight. The reaction is conducted at a temperature in the range from about 30° C. to about 120° C., and preferably in the range from 60° C. to 80° C. The reaction time naturally depends on the strength of the acid used. The higher the strength of the acid used, the shorter the reaction time needed to effect complete oxidation of the double bond. Conversely, the lower the strength of the acid used, the longer the reaction time needed. When operating at a temperature of around 70° C., a reaction time of about four hours to eight hours is commonly used, but a reaction time considerably in excess of this can be employed. The proportion of nitric acid used in this process is usually around thirty to fifty molar equivalents based on the starting cyclopentene derivative, but amounts outside these limits can also be used.

A still further oxidant which is useful for the oxidative cleavage of the double bond of the said compound of formula II is ozone. In this case, the said compound of formula II is dissolved in a suitable solvent and then treated with at least one equivalent of ozone. Solvents which can conveniently be used are those which will dissolve the starting material, but which themselves are inert to the action of ozone. Representative examples of such solvents are ethers, for example, diethyl ether or tetrahydrofuran; chlorinated hydrocarbons, for example, chloroform or methylene chloride; esters, for example, ethyl acetate; and lower alkanols, for example, ethanol or methanol; or mixtures of these solvents can be used. The ozonization is usually conducted at a temperature in the range from about −80° C. to about 30° C., and preferably at about 0° C. At around 0° C. ozone reacts rapidly with the double bond, and ozonization is usually complete within a few minutes after the stoichiometric amount of ozone has been introduced. As will be known by one skilled in the art, typical work-up of the ozonization reaction, for example, by addition of potassium iodide, produces a dialdehyde species. At this point it is then necessary to add a further oxidant to complete the conversion into citric acid or a mono-ester or mono-amide thereof. Many agents are well-known in the art for such a conversion, and in the present case silver oxide or bromine are particularly convenient.

In the instances where the aforementioned oxidative cleavage reaction is applied to a compound of formula II, wherein $R^2$ is lower alkoxy or amino, a further hydrolysis step is required in order to liberate citric acid. A wide variety of hydrolysis methods can be used. Specifically, all those methods described above for the conversion of a compound of formula II, wherein $R^2$ is lower alkoxy or amino, into the compound of formula II, wherein $R^2$ is hydroxy, and which do not adversely affect the product citric acid, can be employed. As will be recognized by one skilled in the art, however, in the particular case wherein nitric acid is chosen as the oxidant, a compound of the formula II, wherein $R^2$ is lower alkoxy or amino, undergoes hydrolysis to a greater or lesser extent during the course of the oxidation. The extent of this concurrent hydrolysis depends on the concentration of nitric acid used and on the temperature and duration of the reaction, and under certain circumstances may be suubstantially complete at the end of the oxidation reaction.

The citric acid produced by the process of this invention can be recovered and purified by a variety of methods. One particularly convenient method utilizes the calcium salt of citric acid. Thus, for example, a reaction medium containing citric acid can be treated essentially as follows: (1) the crude product is isolated using a typical procedure such as solvent evaporation; (2) the crude product is extracted with water giving an aqueous solution of citric acid; (3) an aqueous solution of a water-soluble calcium salt is added; and (4) the precipitate of calcium citrate which forms is filtered off. If desired, the calcium citrate can be converted into free citric acid, for example, by treating it with dilute sulfuric acid. The precipitate of calcium sulfate is then filtered off, leaving an aqueous solution of free citric acid. The acid is recovered by evaporation, or by crystallization techniques.

A further embodiment of this invention concerns the method by which the carbon-carbon double bond of a compound of the formula II, wherein $R^2$ is lower alkoxy or amino, is oxidized to produce a dicarboxylic acid. If desired, this can be carried out utilizing a two-step procedure. In the first step, the said double bond is first hydroxylated to give a 1,2-diol of the formula III, wherein $R^3$ is lower alkoxy or amino, and in the second step the 1,2-diol moiety is cleaved to the required dicarboxylic acid. The hydroxylation step can be carried out using a variety of methods known in the art. A particularly

III convenient method as regards ease of operation involves treatment of the said compound of formula II with osmium tetroxide in an inert solvent such as, for example, diethyl ether, followed by decomposition of the intermediate osmate ester. Cleavage of the 1,2-diol moiety can be achieved by using either nitric acid or potassium permanganate, and by operating under the conditions described above for use with these oxidants. Alternatively, if desired, the 1,2-diol moiety can be cleaved using lead tetraacetate or periodic acid.

The following examples are provided solely for the purpose of illustration. The nuclear magnetic resonance (nmr) spectra were measured at 60 MHz, and peak positions are reported in parts per million (ppm) downfield from tetramethylsilane standard.

EXAMPLE I

1-Hydroxy-3-cyclopentene-1-carbonitrile

To 500 mg. of 3-cyclopentent-1-one, cooled to 0° C. and under an atmosphere of nitrogen, is added 0.2 ml.

of liquid hydrogen cyanide from a precooled syringe. After 2 minutes, 2 drops of a saturated aqueous solution of potassium cyanide are added. The reaction mixture is then stirred at 0° C. for 30 minutes. At this time 2 drops of concentrated sulfuric acid are added, and then the mixture is stirred for a further 30 minutes at 0° C. After removal of the cooling bath, the excess of hydrogen cyanide is removed in vacuo. The oily residue is dissolved in 8 ml. of methylene chloride and then reconcentrated in vacuo, three times. Finally the residue is redissolved in 8 ml. of methylene chloride, the solution is dried using anhydrous sodium sulfate, and then the solution is concentrated in vacuo to give 368.9 mg. of 1-hydroxy-3-cyclopentene-1-carbonitrile as a viscous oil. The infrared spectrum of the product shows a broad absorption band at 3,400 cm$^{-1}$ and a sharp absorption band at 2240 cm$^{-1}$, confirming the presence of a hydroxy and a cyano group, respectively. The nmr spectrum shows absorptions at 5.7 ppm (singlet, olefinic hydrogens), 5.1 ppm (singlet, hydroxy group) and 3 ppm (multiplet, methylene hydrogens).

EXAMPLE II

Methyl 1-Hydroxy-3-cyclopentene-1-carboxylate

A solution of 150 mg. of 1-hydroxy-3-cyclopentene-1-carbonitrile in 10 ml. of anhydrous methanol and 5 ml. of anhydrous diethyl ether is cooled in an ice-bath. The solution is saturated with gaseous hydrogen chloride, then allowed to warm to room temperature and finally set aside overnight. The solution is then concentrated in vacuo to a solid, which is dissolved in approximately 10 ml. of water. After 2¾ hours an aliquot is removed and extracted with methylene chloride. The extract is dried using sodium sulfate, and it is concentrated in vacuo giving methyl 1-hydroxy-3-cyclopentene-1-carboxylate as a yellowish oil. The infrared spectrum of the product (in CDCl$_3$) shows an absorption at 1730 cm$^{-1}$, confirming the presence of an ester function. The nmr spectrum of the product (in CDCl$_3$) shows absorptions at 5.7 ppm (singlet, olefinic hydrogens), 3.8 ppm (singlet, methyl hydrogens) and 3.3–2.2 ppm (singlet superimposed on a quartet, hydroxy group and methylene hydrogens). The remainder of the aqueous solution is worked up analogously to give a further quantity of product. The combined yield is 65.8 mg.

The aqueous phase which has been extracted with methylene chloride is concentrated in vacuo, giving 75.9 mg. of 1-hydroxy-3-cyclopentene-1-carboxylic acid as an amorphous solid.

EXAMPLE III

Following the procedure of Example II, the following esters are produced by replacing the methanol of Example II by the appropriate lower alkanol:

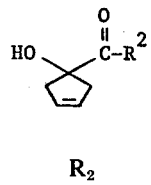

R$_2$

OCH$_2$CH$_3$
OCH$_2$CH$_2$CH$_3$
OCH$_2$CH$_2$CH$_2$CH$_3$
OCH(CH$_3$)$_2$
OCH$_2$CH(CH$_3$)$_2$
OCH(CH$_3$)CH$_2$CH$_3$
OCH$_2$CH$_2$CH$_2$CH$_2$CH$_3$
OCH$_2$CH$_2$CH(CH$_3$)$_2$

EXAMPLE IV

1Hydroxy-3-cyclopentene-1-carboxamide

To 5 ml. of a solution prepared by mixing one part of water and 9 parts of glacial acetic acid, and then cooling to 0°–10° C., is added 300 mg. of 1-hydroxy-3-cyclopentene-1-carbonitrile. To this is then added 5 ml. of a solution prepared by saturating glacial acetic acid with gaseous hydrogen bromide and cooling to 0°–10° C. The resulting mixture is allowed to stand at room temperature overnight. It is then evaporated to dryness in vacuo, and the residue is partitioned between ethyl acetate and 5% sodium bicarbonate solution. The ethyl acetate layer is separated, and then dried using anhydrous magnesium sulfate. Removal of the ethyl acetate by evaporation in vacuo affords 1-hydroxy-3-cyclopentene-1-carboxamide.

EXAMPLE V

1Hydroxy-3-cyclopentene-1-carboxylic Acid

A mixture of 368 mg. of 1-hydroxy-3-cyclopentene-1-carbonitrile and 2 ml. of 6N hydrochloric acid is heated at 100°–110° C. for 2¾ hours. Another 2 ml. of 6N hydrochloric acid is then added, and the mixture is heated for a further 1 hour at 100°–110° C. The reaction mixture is concentrated to dryness in vacuo. The residue is dissolved in diethyl ether and then reconcentrated in vacuo, several times. Finally the residue is extracted several times with methylene chloride, the combined extract are dried using anhydrous sodium sulfate, and then the extracts are concentrated in vacuo. The residue is a gummy solid which is triturated with cyclohexane, filtered, and dried, giving 153 mg. of 1-hydroxy-3-cyclopentene-1-carboxylic acid as a pale yellow solid. The solid melts at 69°–73° C. The infrared spectrum of the product shows an absorption band at 1740 cm$^{-1}$ confirming the presence of a carboxylic acid group. The nmr spectrum (in CDCl$_3$) shows absorption at 7.4 ppm (broad singlet, acid hydrogen and hydroxy hydrogen), 5.7 ppm (singlet, olefinic hydrogens) and 2.9 ppm (quartet, methylene hydrogens).

EXAMPLE VI

A solution of 21.5 mg. of 1-hydroxy-3-cyclopentene-1-carboxylic acid in 15 ml. of methanol is cooled in an ice-bath. A stream of ozone is bubbled through the solution for 5 minutes, followed by a stream of nitrogen for 10 minutes. A few crystals of potassium iodide are then added, and the solution is stirred for a few minutes. To the orange-red solution is then added 0.2 ml. of 10% sodium hydroxide solution, followed by 77.8 mg. of silver oxide. This causes the reaction mixture to turn yellow and a white precipitate forms. The reaction mixture is then stirred for 20–25 minutes, 0.2 ml. of concentrated hydrochloric acid is added, and the mixture is then stirred for an additional 10 minutes. The insoluble material is filtered off, and the solution is concentrated in vacuo to an orange-colored residue. The residue is extracted with acetone, and then the acetone is concentrated in vacuo giving a yellowish gum which is triturated several times with a mixture of methanol and diethyl ether. This finally produces 24.8 mg of an amorphous solid which by thin-layer chromatography and nmr spectroscopy is shown to contain citric acid.

EXAMPLE VII

To a solution of 442.8 mg. of dicyclohexyl-18-crown-6-ether (an item of commerce, available from Aldrich Chemical Company, Inc., Milwaukee, Wisconsin) in 2 ml. of benzene is added 191.2 mg. of potassium permanganate, and the mixture is stirred until a clear solution is obtained. To this solution is added approximately 65 mg. of methyl 1-hydroxy-3-cyclopentene-1-carboxylate dissolved in 3 ml. of benzene. This causes formation of a brown precipitate. After 1 hour the solid is filtered off and washed with more benzene. The solid remaining is extracted with 10 ml. of water, and then the water is extracted with diethyl ether. Finally the pH of the water is adjusted to 1.0 by addition of 6N hydrochloric acid, and the water is freeze-dried. After being stored in the refrigerator for 2 days the residue is extracted with acetone, some insoluble material is filtered off, and the acetone is concentrated in vacuo giving 73.9 mg of a viscous oil. This oil is dissolved in 2 ml. of 3 N hydrochloric acid and the solution is refluxed for 3 hours. The aqueous acid is removed in vacuo, leaving an oil which does not solidify on trituration with diethyl ether. The residue is shown to contain citric acid by nmr spectroscopy, and thin-layer chromatographic comparison with an authentic specimen of citric acid.

EXAMPLE VIII

To 10 ml. of concentrated nitric acid (71% w/v) is added 500 mg. of 1-hydroxy-3-cyclopentene-1-carboxamide in portions at ambient temperatures, with stirring. The temperature of the mixture is then slowly raised to 60°–70° c. The temperature is held at 60°–70° C. for six hours, and then the mixture is allowed to cool to ambient temperature. The nitric acid is evaporated in vacuo, below 30° C., and then to the residue is added 10 ml. of 2N hydrochloric acid. The mixture is refluxed for one hour and then allowed to cool. The aqueous solution is lyophilized to give crude citric acid.

I claim:
1. A compound of formula

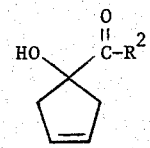

wherein $R^2$ is selected from the group consisting of alkoxy having from one to five carbon atoms and hydroxy.

2. A compound according to claim 1, wherein $R^2$ is the said alkoxy.

3. The compound according to claim 2, wherein $R^2$ is methoxy.

4. The compound according to claim 1, wherein $R^2$ is hydroxy.

* * * * *